(12) United States Patent
Yuan et al.

(10) Patent No.: US 10,080,674 B2
(45) Date of Patent: Sep. 25, 2018

(54) BRANCHED STENT GRAFT, DELIVERY SYSTEM COMPRISING SAME AND METHOD OF FABRICATING SAME

(71) Applicant: MICROPORT ENDOVASCULAR (SHANGHAI) CO., LTD., Shanghai (CN)

(72) Inventors: Zhenyu Yuan, Shanghai (CN); Qing Zhu, Shanghai (CN); Yanbin Gao, Shanghai (CN); Zhonghua Li, Shanghai (CN); Qiyi Luo, Shanghai (CN)

(73) Assignee: MICROPORT ENDOVASCULAR (SHANGHAI) CO., LTD., Shanghai (CN)

( * ) Notice: Subject to any disclaimer, the term of this patent is extended or adjusted under 35 U.S.C. 154(b) by 112 days.

(21) Appl. No.: 14/772,315

(22) PCT Filed: Mar. 4, 2014

(86) PCT No.: PCT/CN2014/072862
§ 371 (c)(1),
(2) Date: Sep. 2, 2015

(87) PCT Pub. No.: WO2014/135070
PCT Pub. Date: Sep. 12, 2014

(65) Prior Publication Data
US 2016/0015536 A1    Jan. 21, 2016

(30) Foreign Application Priority Data
Mar. 4, 2013  (CN) .......................... 2013 1 0068343

(51) Int. Cl.
*A61F 2/07* (2013.01)
*A61F 2/856* (2013.01)
(Continued)

(52) U.S. Cl.
CPC ............... *A61F 2/856* (2013.01); *A61F 2/07* (2013.01); *A61F 2/89* (2013.01);
(Continued)

(58) Field of Classification Search
None
See application file for complete search history.

(56) References Cited

U.S. PATENT DOCUMENTS

| | | | | |
|---|---|---|---|---|
| 2006/0095118 A1* | 5/2006 | Hartley | ..................... | A61F 2/07 623/1.35 |
| 2007/0112410 A1* | 5/2007 | Butaric | ..................... | A61F 2/07 623/1.13 |

(Continued)

FOREIGN PATENT DOCUMENTS

| | | |
|---|---|---|
| CN | 101283937 A | 10/2008 |
| CN | 201510384 U | 6/2010 |

(Continued)

*Primary Examiner* — Thomas J Sweet
*Assistant Examiner* — Megan Wolf
(74) *Attorney, Agent, or Firm* — Muncy, Geissler, Olds & Lowe, P.C.

(57) ABSTRACT

A branched stent graft, a convey system comprising thereof and manufacturing method thereof, the branched stent graft includes a main body (100) and a side branch (200), at least a portion of a lowermost stent section of the side branch (200) closest to the main body (100) is not stitched to the cover of the side branch from a lower end to an upper end, the at least a portion of the lowermost stent section is located on a side of the side branch corresponding to a folding direction of the side branch. After deployed, the branched stent graft has an effective supporting force at the base portion of the side branch. In addition, during the deployment of the stent, the side branch can expand to a maximal extent even when the positioning is slightly inaccurate. Further, vascular stenosis or occlusion will not be caused even when subsequent endothelialization occurs.

4 Claims, 4 Drawing Sheets

(51) Int. Cl.
    *A61F 2/89*     (2013.01)
    *A61F 2/06*     (2013.01)
    *A61F 2/966*    (2013.01)

(52) U.S. Cl.
    CPC ... *A61F 2002/061* (2013.01); *A61F 2002/075* (2013.01); *A61F 2002/9665* (2013.01); *A61F 2220/0075* (2013.01)

(56) References Cited

U.S. PATENT DOCUMENTS

| | | |
|---|---|---|
| 2007/0168013 A1 | 7/2007 | Douglas |
| 2008/0161905 A1 | 7/2008 | Eidenschink |
| 2009/0248135 A1 | 10/2009 | Bruszewski et al. |
| 2010/0268318 A1* | 10/2010 | Glynn ............ A61F 2/07 623/1.13 |
| 2011/0288627 A1* | 11/2011 | Hartley ........... A61F 2/07 623/1.13 |

FOREIGN PATENT DOCUMENTS

| | | |
|---|---|---|
| CN | 201798828 U | 4/2011 |
| CN | 201959033 U | 9/2011 |
| CN | 202122626 U | 1/2012 |
| CN | 102370532 A | 3/2012 |
| CN | 103068345 A | 4/2013 |
| EP | 1673038 A1 | 6/2006 |
| EP | 2522305 A1 | 11/2012 |
| FR | 2970410 A1 | 7/2012 |
| WO | WO 01/74273 A1 | 10/2001 |
| WO | WO 2005034808 A1 | 4/2005 |
| WO | WO 2006065644 A1 | 6/2006 |
| WO | WO 2011/119883 A1 | 9/2011 |

\* cited by examiner

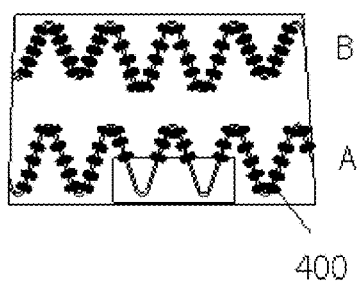
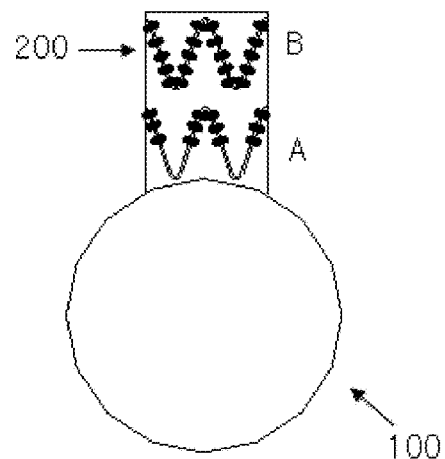
FIG. 5a FIG. 5b
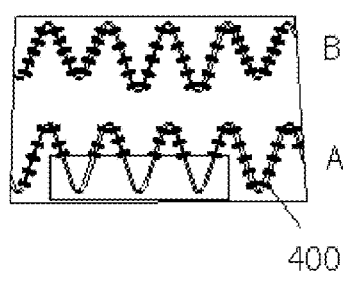
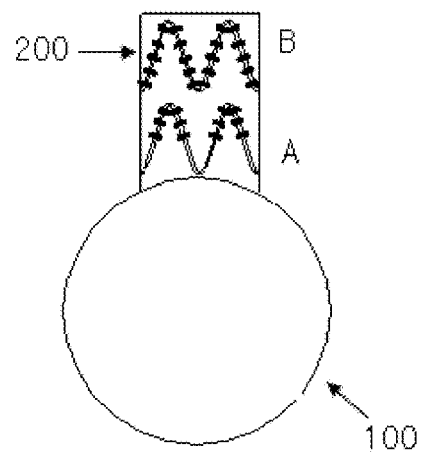
FIG. 6a FIG. 6b

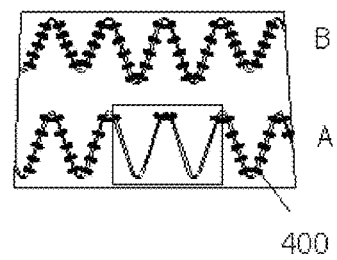
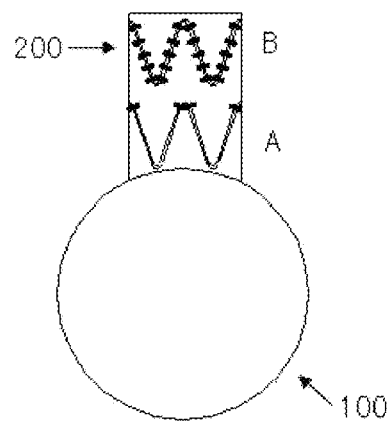
FIG. 7a          FIG. 7b
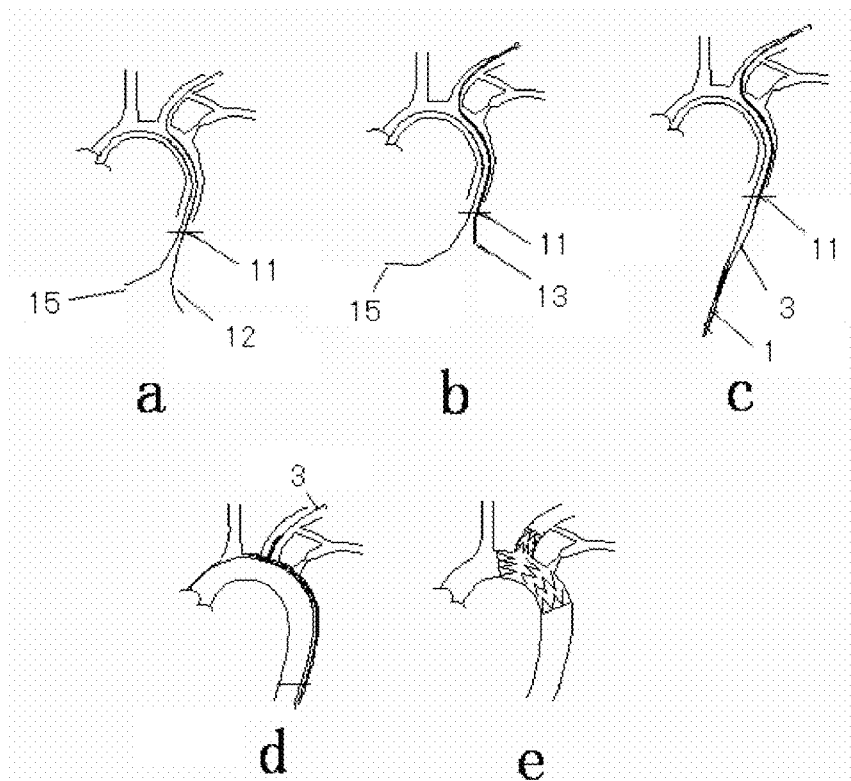
FIG. 8

10,080,674 B2

BRANCHED STENT GRAFT, DELIVERY SYSTEM COMPRISING SAME AND METHOD OF FABRICATING SAME

TECHNICAL FIELD

The present invention relates to medical instruments for minimally invasive interventions and, in particular, to a branched stent graft. In another aspect, the invention relates to a delivery system comprising the branched stent graft. In still another aspect, the invention relates to a method of fabricating the branched stent graft.

BACKGROUND

A major advance in the field of aortic surgery in recent years is the use of stent grafts for the treatment of aortic diseases. Such use generally involves: delivering a stent graft to the aortic lesion with a dedicated delivery system; and then causing the expansion of the stent. Suitable indications of stent grafts include aortic dissections, true aortic aneurysms, false aortic aneurysms, penetrating aortic ulcers, etc. This technology separates aneurysms from the normal blood flow and thereby eliminates the risk of death from hemorrhage caused by ruptured aneurysms or from compression of surrounding tissues and organs by aneurysms, thus greatly reducing operative mortality, postoperative complications, surgical trauma and patient recovery time. Examples of commercially available stent grafts include those marketed under the brands Valiant, Zenith, Relay, Gore, Hercules and Ankura.

However, these commercially available stent grafts are only suitable for the treatment of descending thoracic aortic aneurysms with a 15-mm long normal thoracic aortic aneurysmal wall from the aneurysm or dissection tear to the left subclavian artery. Currently, there is no stent graft available for patients with aortic dissections or aneurysms involving the ascending aorta and the aortic arch, and the patients have to resort to the conventional surgical approach or the chimney technology, as shown in FIGS. 1a and 1b.

With the development of minimally invasive technologies, some branched stent grafts have been proposed. From a structural point of view, such branched stent grafts can not only be used to treat the diseases involving the ascending aorta and aortic arch, but also to replace those currently applied in the practical use for treating descending aortic diseases. They enable more safe and reliable treatment by overcoming some disadvantages of the existing stent grafts and by reducing surgical complications.

Chinese Utility Model Publication No. CN201020524397 disclosed a thoracic aortic stent structure including a main vascular prosthesis and one to three branches disposed on the main vascular prosthesis. Chinese Utility Model Publication No. CN200920218598 disclosed an aortic endoluminal stent mainly for use in repair of vascular diseases. The aortic endoluminal stent is essentially consisted of a main body, which is covered with a cover or a braid layer, and a side branch. The main body is composed of a plurality of sections which are interconnected to one another in such a manner that the main body has a curved contour capable of facilitating the repair of a branched portion of a curved vessel. U.S. Pat. No. 7,914,572 disclosed a stent graft with a side branch, in which a main stent graft has a fenestration to which the side branch is so stitched that it can partially extend into the main stent graft. U.S. Pat. No. 7,314,483 disclosed a stent graft with a branch leg, wherein the branch leg is anchored to a main stent graft.

A branched stent graft is typically fabricated in the following manner. At first, a metal material (e.g., NiTi wires or stainless steel wires) is used to produce stents, each of which is subsequently stitched onto a cover (e.g., made of polytetrafluoroethylene, nylon, polyester, terylene or polypropylene) using a polymeric suture (e.g., made of polytetrafluoroethylene, nylon, polyester, terylene or polypropylene), so as to respectively form a main body 10 and a side branch 20 of the stent graft, as shown in FIG. 2a. The main body 10 and the side branch 20 are then stitched together, as shown in FIG. 2b. Typical dimensions of a branched stent graft include: the main body 10 has a length of 60-210 mm and a diameter of 24-50 mm, and the side branch 20 has a length of 10-50 mm and a diameter of 6-18 mm. Further, the side branch 20 should be adjoined to the main body 10 in such a way that a length L of the cover is reserved at the joint to ensure that the assembled branched stent graft can be crimped into an outer sheath 4 of a delivery system 1, as shown in FIG. 2b.

With the main body 10 and side branch 20 have been assembled, they are inserted into the outer sheath 4 of the delivery system 1. In this process, the main body 10 is first contracted to a diameter similar to that of the outer sheath 4 by using contraction lines 30. The side branch 20 is then received in a branch sheath 7 and folded together with the branch sheath 7 towards a proximal end of the main body 10 such that the side branch 20 is parallel to the main body 10. In this configuration, the whole branched stent graft can be positioned inside the sheath 4, as shown in FIG. 3b. Each stent section of the side branch 20 is stitched to the cover in a manner like the section B shown in FIG. 5a, i.e., being entirely stitched from end to end. After this process, a distance L from the side branch 20 to the main body 10 must be ensured to at least exceed a radius of the side branch 20. Otherwise, the side branch 20 cannot be folded to an orientation that is parallel to the main body 10 and thus cannot be received in the outer sheath 4.

However, currently, no assessment has ever been conducted to evaluate the safety and efficacy of these conventional branched stent grafts. In particular, as noted above, in order to facilitate the assembly and deployment, a length L of several millimeters (generally greater than 3 mm) of the cover, on which no stent section is stitched, is arranged between the side branch 20 and the main body 10. One reason for this design is that, if the side branch 20 and the main body 10 are stitched together without the cover being reserved therebetween, in the assembled state, it is impossible to configure the side branch 20 to make it parallel to the main body 10, thus failing the positioning of the side branch 20 in the outer sheath 4 of the delivery system 1. Therefore, all the existing branched stent grafts have such a cover section with length L between the main body and the side branch. That is, the main body and the side branch are interconnected only by the flexible cover section not being supported by any stent section. This tends to cause narrowing of the side branch at its base portion, as well as an occlusion thereof in case of inaccurate positioning in the deployment process. Further, even after such a stent has been successfully deployed, it is likely that endothelialization occurs and fills the gap between the cover section and the vessel wall and thus causes vascular stenosis or occlusion.

SUMMARY OF THE INVENTION

Therefore, it is an objective of the present invention to overcome the above-described problems of the conventional branched stent grafts. In a first aspect, the invention accordingly provides an improved branched stent graft, in which, a distance from a proximal (i.e., nearer to the heart) end of a side branch to a main body is substantially zero, while still allowing the side branch to be loaded in the same conventional parallel configuration and ensuring normal expansion thereof under regular deployed conditions. In addition, even when a small amount of deviation of the side branch occurs during the deployment process, as the side branch is stent-supported throughout the whole length, its narrowing is minimized, which results in an improved surgery success rate.

According to the present invention, the branched stent graft includes a main body and a side branch, each of the main body and the side branch includes a cover and a stent consisting of stent sections, at least a portion of a lowermost stent section of the side branch closest to the main body is not stitched to the cover of the side branch from a lower end to an upper end, the at least a portion of the lowermost stent section is located on a side of the side branch corresponding to a folding direction of the side branch. With this design, when the side branch is folded, the portion of the stent section, that is not stitched to the cover of the side branch, is detachable from the cover and thereby allows the side branch to be placed in the outer sheath in a configuration parallel to the main body. In addition, during the release of the stent, the stent section can still resume its original shape to exert a supporting function. Therefore, the narrowing of the base portion of the side branch can be avoided.

According to embodiment of the present invention, only an upper half or an upper apex of the portion of the lowermost stent section located on the side of the side branch corresponding to the folding direction is stitched to the cover of the side branch. In addition, according to embodiment of the present invention, in the lowermost stent section of the side branch closest to the main body, at least a portion of each of two or three consecutive V-shaped elements on the side of the side branch corresponding to the folding direction is not stitched to the cover of the side branch from the lower end to the upper end.

When deployed, the branched stent graft according to the present invention can have an effective supporting force at the base portion of the side branch. In addition, during the deployment of the stent, the side branch can expand to a maximal extent even when the positioning is slightly inaccurate. Further, vascular stenosis or occlusion will not be caused even when subsequent endothelialization occurs.

In a second aspect, the present invention provides a method of fabricating a branched stent graft. According to the invention, the method includes the steps of: producing stents respectively for a main body and a side branch from a metal material; and stitching the stents onto respective covers with sutures to form the main body and the side branch, wherein in lowermost stent section of the side branch closest to the main body, the side branch is so formed that at least a portion of one of the stent sections of the side branch corresponding to the folding direction is not stitched to the cover of the side branch, and the side branch is so stitched to the main body that the portion of the one of the stent sections of the side branch corresponding to the folding direction, that is not stitched to the cover of the side branch from a lower end to an upper end.

According to embodiment of the present invention, the side branch is so formed that only an upper half or an upper apex of the portion of the lowermost stent sections located on the side of the side branch corresponding to the folding direction is stitched to the cover of the side branch. In addition, according to embodiment of the present invention, in the lowermost stent section of the side branch closest to the main body, the side branch is so formed that at least a portion of each of two or three consecutive V-shaped elements on the side of the side branch corresponding to the folding direction is not stitched to the cover of the side branch from the lower end to the upper end.

By stepwise stitching, the method according to the present invention can result in a normally mountable and releasable branched stent graft with no deterioration in performance.

In a third aspect, the present invention provides a delivery system incorporating a branched stent graft as defined above.

The present invention is applicable in the treatment of ascending aortic aneurysms, aortic arch aneurysms, descending aortic aneurysms and aortic dissections. With the delivery system, the stent according to the present invention can be deployed at the same time to one or more of the aorta, the left subclavian artery, the left common carotid artery, the innominate artery, and their branching vessels, to treat a larger scope of indications including dissections and aneurysms involving the ascending aorta, aortic arch and the descending aorta.

BRIEF DESCRIPTION OF THE DRAWINGS

The features and advantages of the present invention will become apparent upon reading the following detailed description of embodiments of the invention, in conjunction with the accompanying drawings, in which:

FIGS. 5a to 5b are schematics illustrating stitching of a side branch of a branched stent graft according to one embodiment of the present invention.

FIGS. 6a to 6b are schematics illustrating stitching of a side branch of a branched stent graft according to another embodiment of the present invention.

FIGS. 7a to 7b are schematics illustrating stitching of a side branch of a branched stent graft according to another embodiment of the present invention.

FIG. 8 schematically illustrates a surgical procedure for implanting a branched stent graft according to the present invention.

LIST OF REFERENCE NUMERALS

| | |
|---|---|
| 1 | Delivery System |
| 2 | Control Guidewire |
| 3 | Branch Guidewire |
| 4 | Outer Sheath |
| 5 | Push-out Tube |
| 6 | Inner Tube |
| 7 | Branch Sheath |
| 10 | Main Body |
| 11 | Femoral Artery Puncture |
| 12 | Left Common Carotid Artery Guidewire |
| 13 | Left Common Carotid Artery Catheter |

| | |
|---|---|
| 15 | Super-stiff Guidewire |
| 20 | Side Branch |
| 30 | Contraction Lines |
| 100 | Main Body |
| 200 | Side Branch |
| 300 | Contraction Lines |
| L | Length of Cover |
| A, B | Stent Sections |

DETAILED DESCRIPTION

Embodiments of the present invention are described below with reference to the accompanying drawings.

In order to facilitate the description, the terms "folding direction", "proximal end", "distal end", "upper end" and "lower end" are used in this specification, in which, the term "proximal end" refers to an end nearer to the heart, and the term "distal end" means an end farther away from the heart; when used with respect to a stent of a side branch, the term "lower end" denotes an end of the stent nearer to a main body, and the term "upper end" means an end of the stent farther away from the main body; and the term "folding direction" refers to, when the side branch has been folded to an orientation parallel to the main body during its insertion into the sheath, a direction of the side branch (either toward a proximal end or a distal end of the main body).

In embodiments of the present invention, each of the branched stent grafts is described to have one side branch. However, it is obvious for those skilled in the art that it is still possible for each of the branched stent grafts to have more than one side branch. Additionally, while in embodiments of the present invention, in the lowermost stent section of the side branch closest to the main body, two or three consecutive V-shaped elements on one side of the side branch corresponding to the folding direction are described to be partially or entirely left unstitched onto the cover of the side branch from the lower end to the upper end, it is obvious for those skilled in the art that other number of V-shaped elements is also possible.

Figure 4:
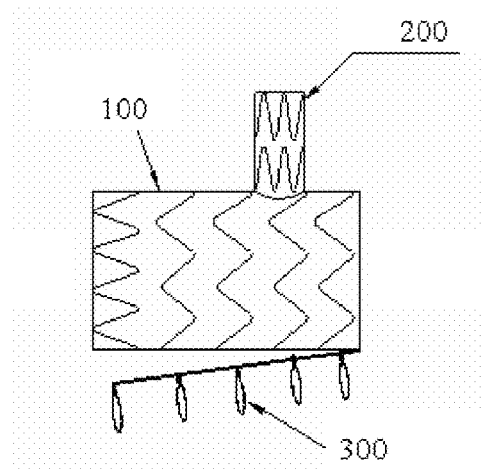
FIG. 4 is a schematic illustration of a branched stent graft according to the present invention.

FIG. 4 shows a branched stent graft according to an embodiment of the present invention, including a main body 100 and a side branch 200. The stent of the side branch 200 is in close proximity to the main body 100. That is, between the main body and the side branch, there is essentially no cover portion not being supported by a stent section. In addition, as also detailed below, at least a portion of a lowermost stent section of the side branch 200 closest to the main body 100 is not stitched to the cover of the side branch 200 from a lower end to an upper end, the at least a portion of the lowermost stent section is located on a side of the side branch 200 corresponding to a folding direction of the side branch 200.

In this embodiment, the main body 100 has a length of 100 mm and a diameter of 36 mm, and the side branch 200 has a length of 30 mm and a diameter of 10 mm. Contraction lines used in this embodiment have a semi-perimeter of 20 mm.

Figure 1A:
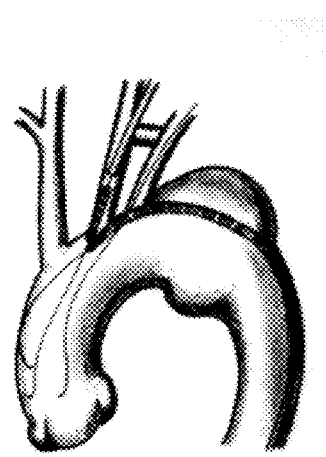
FIGS. 1a and 1b schematically illustrate the treatment of an aortic disease using the conventional chimney technology.
Figure 1B:
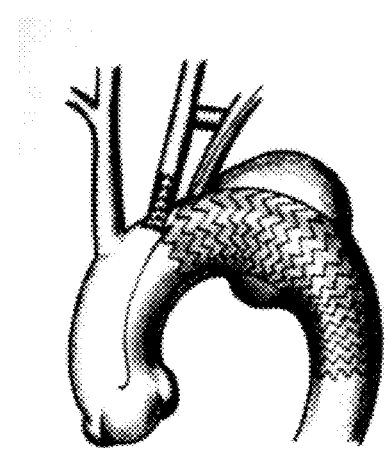
Figures 2A, 2B:
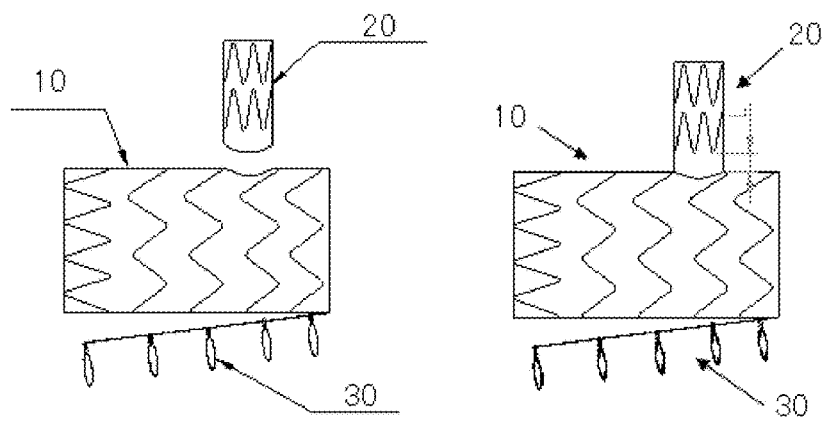
FIGS. 2a to 2b are schematic illustrations of a conventional branched stent graft.
Figure 3A:
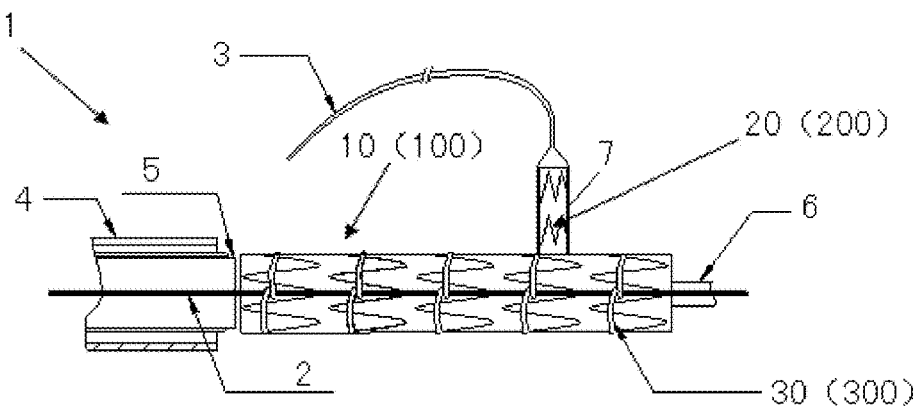
FIGS. 3a to 3b diagrammatically depict a stent according to the present invention before and after it is crimped into an outer sheath of a delivery system.
Figure 3B:
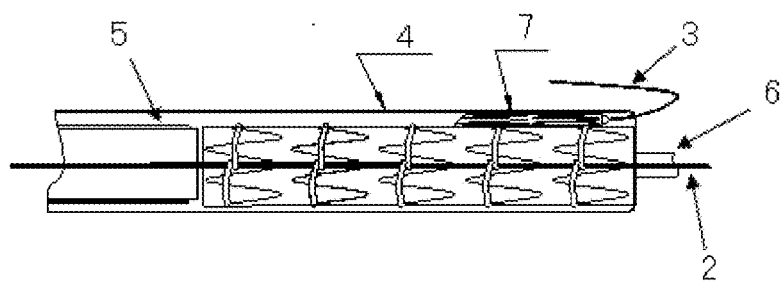

When to assemble a delivery system 1, with similarity to the conventional approach, the main body 100 is first contracted by the contraction lines 300 to a diameter similar to a diameter of the outer sheath 4. The side branch 200 is then inserted in the branch sheath 7, as shown in FIG. 3a. Afterward, the side branch 200 is folded together with the branch sheath 7 toward the proximal end and finally into a configuration parallel to the main body 100. At last, the branched stent graft is entirely positioned inside the sheath 4, thereby completing the assembly of the delivery system 1, as shown in FIG. 3b. Since at least a portion of the stent of the side branch 200 is at least partially (half or the whole) left unstitched on the cover thereof in a direction from the lower end to the upper end, like the stent section A shown in FIGS. 5a, 6a and 7a, the unstitched stent portion can move freely without being restricted by the cover during the folding of the side branch 200, thereby allowing the side branch 200 to be loaded together with the main body 100 inside the outer sheath 4 in the parallel configuration.

The delivery system 1 may further include a control guidewire 2, a branch guidewire 3, a push-out tube 5 and an inner tube 6. In order to deploy the branched stent graft, the branched stent graft is pushed out and released from the outer sheath 4 by the push-out tube 5, as shown in FIG. 3a. All of these are known to those skilled in the art, and further description thereof is omitted herein.

A description of the fabrication of the branched stent graft is provided below.

Example 1

FIGS. 5a to 5b show a branched stent graft fabricated by a method according to the present invention, with a side branch 200 having lowermost portions of two V-shaped elements of a stent section nearest to a main body 100 left unstitched.

In the fabrication process, a metal material for medical use (e.g., NiTi wires) is used to produce stents with wave patterns, each of which are then stitched with polyester sutures onto a polyester cover, thereby forming the main body 100 and the side branch 200, wherein the stitching of the stent section of the side branch 200 nearest to the main body 100 is conducted in the manner described above. Afterward, the side branch 200 is stitched to the main body 100 by sutures, and the unstitched elements are located on one side of the side branch corresponding to the folding direction.

The formed branched stent graft is then placed in the outer sheath 4 to complete the delivery system 1. During use, the branched stent graft is deployed in the human body, as described below. The branched stent graft is used to treat an aneurysm or dissection by separating the aneurysm from the blood flow.

Example 2

FIGS. 6a to 6b show another branched stent graft fabricated by a method according to the present invention. A side branch 200 has lowermost portions of three V-shaped elements of a stent section nearest to a main body 100 left unstitched. The side branch 200 is stitched to the main body 100, with the unstitched elements located on one side of the side branch corresponding to the folding direction.

Example 3

FIGS. 7a to 7b show another branched stent graft fabricated by a method according to the present invention. A side branch 200 has two V-shaped elements of a stent section nearest to a main body 100 only stitched at their apexes. The remainder of the elements is left unstitched. The side branch 200 is stitched to the main body 100, with the unstitched elements located on one side of the side branch corresponding to the folding direction.

As the branched stent grafts of Examples 2 and 3 both differ from that of Example 1 only in the stitching of the side branch 200 and are identical thereto in the remaining structure and fabrication method, further description is omitted herein.

FIG. 8 shows use of a branched stent graft according the present invention. In the illustrated embodiment, a lesion is first bypassed and the left subclavian artery is then ligated, followed by deploying the side branch 200 in the left common carotid artery. In the surgical procedure, a super-stiff guidewire 15 of the delivery system 1 is introduced from a femoral artery puncture 11. A left common carotid artery guidewire 12 is then introduced from the left common carotid artery guidewire, and advanced until it protrude out of the femoral artery puncture 11, as shown in FIG. 8a. After that, a left common carotid artery catheter 13 is introduced through the left common carotid artery guidewire 12, thereby forming a passageway. The left common carotid artery guidewire 12 is then retrieved, as shown in FIG. 8b. Next, a branch guidewire 3 of the delivery system 1 is introduced from the left common carotid artery catheter 13 and is advanced until it travels out from the left common carotid artery, as shown in FIG. 8c. At the same time, the main body 100 is advanced along the super-stiff guidewire 15 to the aortic arch, followed by drawing the side branch 200 into the left common carotid artery along the branch guidewire 3, as shown in FIG. 8d. After the side branch 200 has been positioned, a control guidewire 2 is extracted, causing the contraction lines 300 to gradually loosen node-by-node with the extracting of the control guidewire 2. When this happens, the main body 100 radially expands against the vessel wall. With the release of the main body 100 completed, the side branch 200 is released by drawing the branch guidewire 3. At last, the delivery system 1 is retrieved from the body, and the deployment of the branched stent graft is completed.

As described above, after deployed, the branched stent graft according to the present invention can have an effective supporting force at the base portion of the side branch. In addition, during the deployment of the stent, the side branch can expand to a maximal extent even when the positioning is slightly inaccurate. Further, vascular stenosis or occlusion will not be caused even when subsequent endothelialization occurs.

It will be understood by those skilled in the art that the above description is merely illustrative. Various modifications and variations may be made by those skilled in the art that without departing from the spirit and scope of the invention.

What is claimed is:

1. A branched stent graft, comprising a main body and a side branch stitched to the main body, each of the main body and the side branch comprising a cover and a stent consisting of stent sections, wherein a portion of a lowermost stent section of the side branch closest to the main body is not stitched to the cover of the side branch from a lower end to an upper end, one or more of the stent sections of the side branch other than the lowermost stent section being stitched to the cover of the side branch, the portion of the lowermost stent section located on a side of the side branch corresponding to a folding direction of the side branch, another portion of the lowermost stent section of the side branch that does not correspond to the folding direction stitched to the cover of the side branch from the lower end to the upper end, wherein a lower end of the side branch corresponds to an end of the side branch connected to the main body, and an upper end of the side branch corresponds to an end of the side branch extending away from the main body, and wherein none of the stent sections of the main body extends around the side branch.

2. The branched stent graft as claimed in claim 1, wherein the lowermost stent section is stitched only on an upper half or an upper apex of the lowermost stent section of the side branch corresponding to the folding direction to the cover of the side branch.

3. The branched stent graft as claimed in claim 2, wherein in the lowermost stent section of the side branch closest to the main body, each of two or three consecutive V-shaped elements on the side of the side branch corresponding to the folding direction is not stitched to the cover of the side branch from the lower end to the upper end.

4. The branched stent graft as claimed in claim 1, wherein in the lowermost stent section of the side branch closest to the main body, at least a portion of each of two or three consecutive V-shaped elements on the side of the side branch corresponding to the folding direction is not stitched to the cover of the side branch from the lower end to the upper end.

* * * * *